United States Patent [19]

Rife

[11] Patent Number: 4,529,308

[45] Date of Patent: Jul. 16, 1985

[54] SPECTROPHOTOMETER APPARATUS AND METHOD INCLUDING SCALE DRIFT CORRECTION FEATURE

[75] Inventor: Douglas D. Rife, Sterling, Va.

[73] Assignee: Hunter Associates Laboratory, Inc., Reston, Va.

[21] Appl. No.: 383,295

[22] Filed: May 28, 1982

[51] Int. Cl.³ .............................................. G01J 3/42
[52] U.S. Cl. ...................................... 356/323; 356/448
[58] Field of Search ...................... 356/319, 323–325, 356/433, 434, 445, 447, 448, 436

[56] References Cited

U.S. PATENT DOCUMENTS

| | | | |
|---|---|---|---|
| 3,516,746 | 6/1970 | Shibata et al. | 356/319 |
| 3,666,362 | 5/1972 | Chance . | |
| 3,854,050 | 12/1974 | Peterson et al. | 250/429 |
| 3,999,062 | 12/1976 | Demsky et al. | 250/227 |
| 4,014,612 | 3/1977 | Atwood et al. . | |
| 4,063,822 | 12/1977 | de Jong et al. . | |
| 4,076,421 | 2/1978 | Kishner . | |
| 4,165,180 | 8/1979 | Failes | 356/310 |
| 4,178,917 | 12/1979 | Shapiro | 356/39 |
| 4,247,202 | 1/1981 | Failes | 356/310 |
| 4,260,263 | 4/1981 | Kummer | 356/448 |
| 4,320,970 | 3/1982 | Dowben et al. | 250/458.1 |

FOREIGN PATENT DOCUMENTS 15170 9/1980 European Pat. Off. ............ 356/325
712687 1/1980 U.S.S.R. .............................. 356/436.

Primary Examiner—F. L. Evans
Attorney, Agent, or Firm—Cushman, Darby & Cushman

[57] ABSTRACT

Spectrophotometer apparatus and method is disclosed which utilizes a totally unobstructed test light flux channel in combination with a periodically occluded reference light flux channel. The outputs of the test and reference channels are mixed and presented to a common light analyzing device from which successive timed-multiplexed measurements can be used to provide spectrophotometric data automatically corrected for drift in critical parameter values associated with the common source and/or light analyzing device. For example, by subtracting light flux measurements obtained during occluded periods from those obtained when the reference channel is not occluded, a measurement can be derived for the light flux passing through the reference channel alone. This derived measurement can then be used to drift-correct measurements made on the light flux coming thorugh the test channel alone when the reference channel is occluded. Comparison of successive light flux measurements made under similar conditions (i.e., when the reference channel is occluded or when it is not occluded) can also be made to ensure that the specimen to be tested has settled into a relatively static condition where meaningful measurements can be made.

45 Claims, 5 Drawing Figures

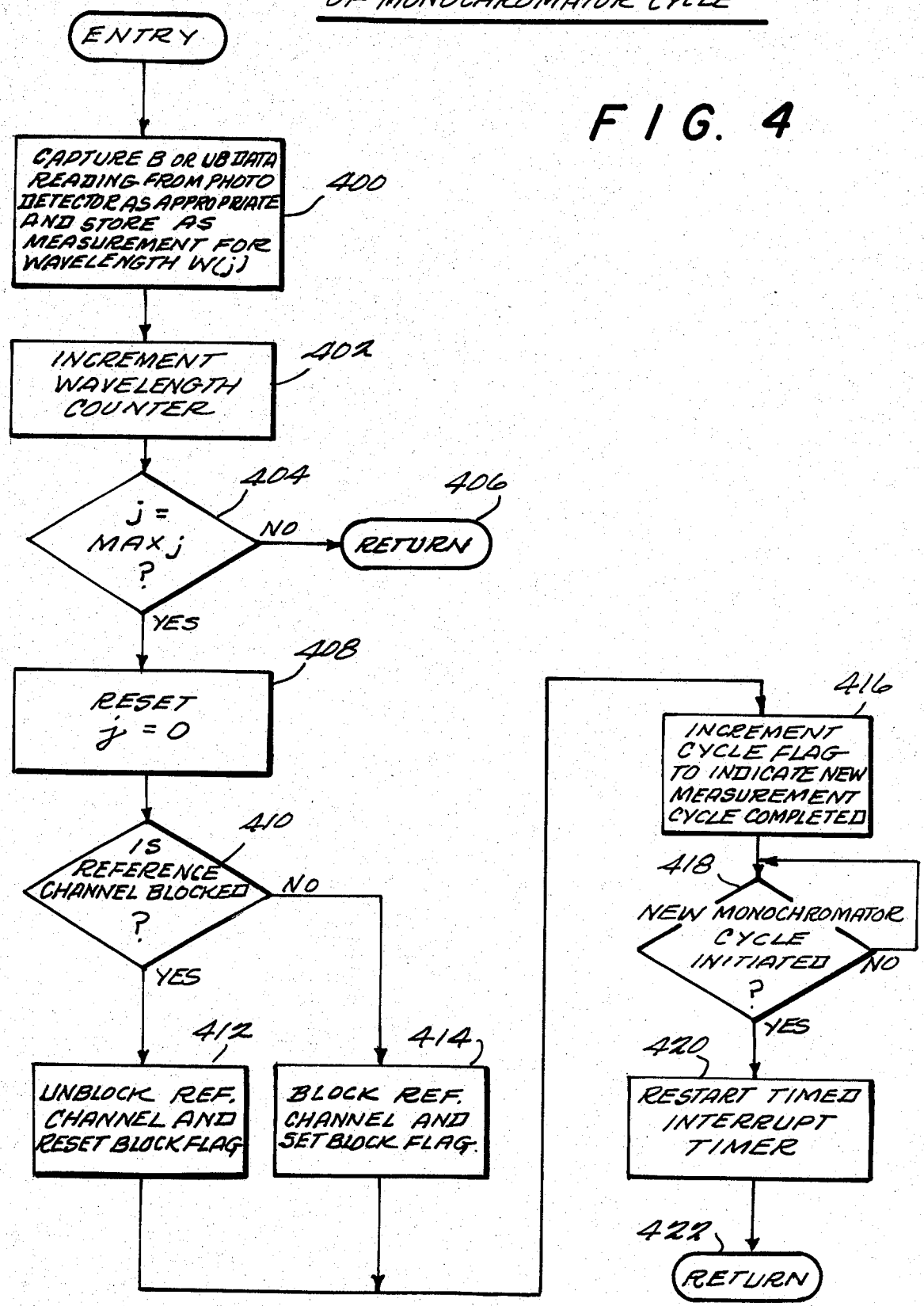

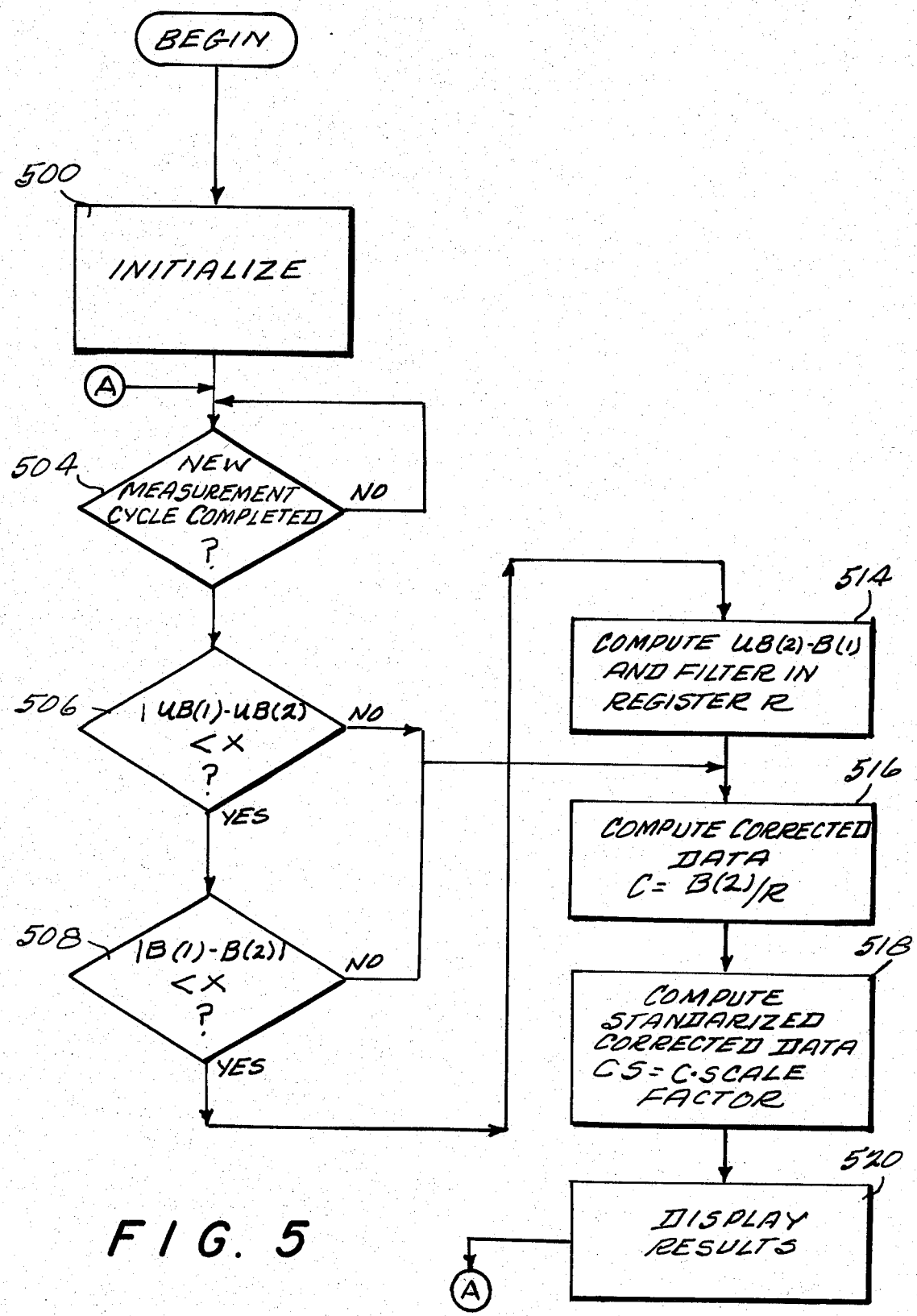

SPECTROPHOTOMETER APPARATUS AND METHOD INCLUDING SCALE DRIFT CORRECTION FEATURE

This invention is generally directed to spectrophotometer apparatus and method. In particular, it relates to automatic correction for variations in the critical parameters of the common light source and light analyzing devices typically used in single beam spectrophotometers which are used to measure the transmittance and/or reflectance of specimen materials.

Spectrophotometers of many difference sorts are well known in the prior art. In general, they involve the measurement of light transmittance through and/or light reflectance from material specimens that are temporarily inserted into or otherwise affixed with respect to a spectrophotometer for measurement purposes. Typically, such analysis is conducted at many different light wavelengths (or ranges of wavelengths) with various techniques being employed to control the wavelength of light emanating from a light source and/or the wavelength of light ultimately incident upon a photosensitive electrical transducer.

Since the measured electrical signal representing transmitted and/or reflected light from the specimen is necessarily a function of the quantity of light flux at that particular wavelength generated by the light source, the efficiency at that particular wavelength of a monochromator (or of other optical devices included in the light paths), the sensitivity at that particular wavelength of a photodetector, etc., and since these critical parameter values of the light source and/or light analyzing devices often change as a function of ambient temperature, aging and other known or unknown causes, it is also well recognized that corrections must be made for these variations if one is to obtain truly accurate quantitative data on the transmittance/reflectance of a specimen material.

Typically, a test light conducting channel is periodically interrupted and a reference light conducting channel is synchronously opened so as to provide quantitative reference light flux measurements which may be used for calculating drift-corrected data values. However, such techniques require synchronous and alternate occlusion of both the test channel and a reference light flux conducting channel. This typically requires relatively rapid mechanical movements of relatively large mechanical structures. Other drift-correction techniques sometimes employ a separate parallel reference channel with its own photodetector. However, these techniques not only require additional apparatus components, they usually rest on the assumption that two given photodetectors have similar sensitivity variations as a function of wavelength, temperature, etc.

Some examples of typical prior art spectrophotometer apparatus and method are illustrated by the following prior issued U.S. patents:

U.S. Pat. No. 3,666,362—Chance (1972)
U.S. Pat. No. 3,854,050—Peterson et al. (1974)
U.S. Pat. No. 3,999,062—Demsky et al. (1976)
U.S. Pat. No. 4,014,62—Atwood et al. (1977)
U.S. Pat. No. 4,063,82—de Jong et al. (1977)
U.S. Pat. No. 4,076,421—Kishner (1978)
U.S. Pat. No. 4,165,180—Failes (1979)
U.S. Pat. No. 4,178,917—Shapiro (1979)
U.S. Pat. No. 4,247,202—Failes (1981)
U.S. Pat. No. 4,320,970—Dowben et al. (1982)

Demksy et al appear to alternately take pure test and pure reference readings. Atwood et al use two separate detectors for the test and reference channels as do de Jong et al, Shapiro, Dowben et al, Chance and Kishner. Failes uses a common detector but appears to alternately chop both the reference and test channels in a manner similar to Demsky. Peterson et al also seem to alternately view only a sample or reference cell while a separate detector is used to monitor the light source.

A typical prior art single beam spectrophotometer utilizes a source of polychromatic illumination (covering the wavelength ranges of interest) directed toward a specimen—by use of conventional projection optics. After modification by reflection or transmittance from or through the specimen, the resulting light flux is typically collected by conventional viewing optics and presented to a monochromator. The monochromator then separates the light into its component wavelengths either sequentially or simultaneously and presents the resultant light flux to either a single detector or an array of detectors respectively. The light detector(s) then generates an analog electrical signal proportional to the light flux incident thereon at a particular wavelength. Typically, the analog electrical output of the light detector(s) is then conventionally converted to a digital representation and captured by a suitably programmed digital data processor.

One important function of the digital data processor in such prior art spectrophotometers is to scale the raw captured data relative to a perfect 100% reflecting or transmitting primary standard specimen. Because of difficulty in constructing and/or maintaining primary reflectance standards, a secondary standard having less than 100% reflectance is normally used to standardize the instrument. In a transmittance measurement mode, standardization is less difficult because the standard "specimen" is simply represented by the absence of any specimen.

Typically, such absolute standardization is accomplished by installing the standard specimen in the instrument and then reading the raw (unscaled) reflectance/transmittance values at each wavelength of interest. The scaling factors S are then computed at each wavelength by the formula $S = T_r/R_r$ where $T_r$ represents the true known reflectance/transmittance of the standard specimen and $R_r$ represents the raw measured reflectance/transmittance of the standard specimen. These calculated scaling factors for each wavelength are then stored in the memory of the data processing apparatus and subsequently used to compute standardized measurement values by multiplying the actually measured data value by the previously stored scale factor. This general type of standardization computation is conventional in and of itself and its usage is contemplated in the exemplary embodiment of this invention now being described.

However, a common problem with single beam spectrophotometers is that the standardization scale factors previously described actually change as a function of time, temperature and other factors thus often necessitating quite frequent re-standardizaton with the standard specimen so as to maintain acceptably accurate results. In large part, the variations in the scale factor are believed to be due to relatively slow drifts in critical parameter values associated with the light source, monochromator, detectors, etc. Furthermore, the direction and magnitude of such drift are often different for different wavelengths.

This invention provides apparatus and method for automatically and continuously correcting for such relatively slow drifts in the scale factors.

The present invention is based on the discovery of novel apparatus and method which is believed to represent a considerable pratical improvement over any of such prior art approaches. In brief summary, during any given complete measurement cycle, this invention provides a continuously unobstructed test light flux channel in combination with a periodically occluded reference channel. The outputs of the test and reference channels are mixed and presented to a common monochromator from which successive measurements are used to provide spectrophotometric data which is automatically corrected for drift in the values of critical parameters associated with a common light source and/or light analyzing devices.

Stated somewhat differently, this invention provides an arrangement where drift-corrected spectrophotometer measurements are made in a relative manner using but a single light source and a single monochromator. Readings obtained from the test or sample channel alone are compared with a substantially contemporaneous (albeit time-multiplexed) reading obtained from a combined sample/reference channel. In this manner, any drift in the common sample/reference channel elements (e.g, light source, diffuser, light scrambler, monochromator, detector, etc.) can be automatically compensated. Absolute calibration to a standard reference level still must be made by other conventional techniques. Thus, the reference channel is never viewed in isolation. Rather, it is only periodically mixed with the test channel and a difference calculation is made to obtain a derived measurement of the light flux passing through the reference channel alone. This derived measurement can then be used to obtain drift-corrected data readings.

Perhaps yet another way of describing this invention is to note that while the normal test channel is continuously "on," the reference channel is periodically occluded. The outputs of the reference and test channels are continuously mixed before input to a common detector. Calculations made based upon successive detector readings taken while the reference channel is (i) occluded and (ii) not occluded are then sufficient to obtain resultant test data that is automatically corrected for drift errors.

The presently preferred exemplary embodiment of apparatus for practice of this invention (as described in more detail below) includes a common light source and light analyzer device. A specimen testing light conducting channel emanates from the common light source and terminates in the vicinity of the light analyzing device. This test channel typically includes conventional specimen holding apparatus for introducing a test specimen into its continuously conductive light path. A separate reference light conducting channel also emanates from the same light source and terminates it the vicinity of the same light analyzer. However, the reference channel includes a blocking mechanism for temporarily occluding its light conducting path during a light analyzing cycle.

The exemplary light analyzing device includes a microprocessor-based data processing and control apparatus for quantitatively detecting and measuring light flux input to the analyzer. It subtracts quantitative measurements obtained when the reference channel is occluded from those obtained when the reference channel is not occluded (for similar light wavelengths, of course) so as to derive a quantitative measure of the light flux being conducted through the reference channel alone—even though the light analyzer is never actually presented with light from the reference channel alone. This derived quantitative measure is then used for drift-correcting test measurement data obtained by the analyzer when the reference channel is occluded (i.e., when the analyzer is presented with light flux from the test channel alone).

The exemplary embodiment employs a polychromatic light source in conjunction with a scanning monochromator at the entrance of the light analyzer device so as to pass only a selected wavelength or band of wavelengths therethrough to a photodetector. The data processing and control means is electrically connected so as to receive quantitative electrical measurement signals emanating from the photodetector and to also control the blocking mechanism in the reference channel.

If the monochromator or other light analyzing device used in this embodiment has variations in its sensitivity, efficiency or other essential attributes with respect to spatial distribution of light flux within its input aperture, then a light scrambling mechanism is preferably employed prior thereto for spatially mixing light flux from both the test and reference light conducting channels.

In the exemplary emobdiment, the reference light conducting channel is, in large part, formed by a serially arranged pair of fiber optic light conduits having a pair of respective aligned ends which define a gap through which light may be permitted to pass or not to pass by interposition of a light blocking mechanism. For example, an opaque blade attached to the movement of a galvanometer can be employed to provide a physical light blocking member that can be selectively moved into and out of such a gap upon electrical activation.

In the exemplary embodiment, for any given measurement wavelength, the light analyzing devices capture data B (representing the quantity of light flux received when the reference channel is blocked) and data UB (representing the quantity of light flux received when the reference channel is unblocked). Thereafter, drift-corrected measurement data C for that wavelength is calculated in accordance with the formula $C = B/(UB-B)$. Preferably, such data is taken during cyclic sample periods (when the reference channel is blocked and when it is unblocked) and such quantitative analysis is inhibited unless data collected during successive similar portions of such cyclic sample periods agree within a predetermined tolerance value that is greater than the expected noise of the system. It is also preferred to average together at least the derived data (UB-B) over plural of the most recent cyclic sample periods (e.g., a running average).

These as well as other objects and advantages of this invention will be better understood by careful study of the following description of the presently preferred exemplary embodiment of apparatus for practicing this invention taken in conjunction with the accompanying drawings, of which:

FIG. 4 is a flow diagram of an exemplary timed interrupt program which may be used in conjunction with the microprocessor-based light analyzer and control circuits in the embodiment of FIGS. 1 and 3; and FIG. 5 is a flow chart of an exemplary main program that may be used in conjunction with the microprocessor-based light analyzer and control circuits shown in the embodiment of FIGS. 1 and 3.

Figure 1:
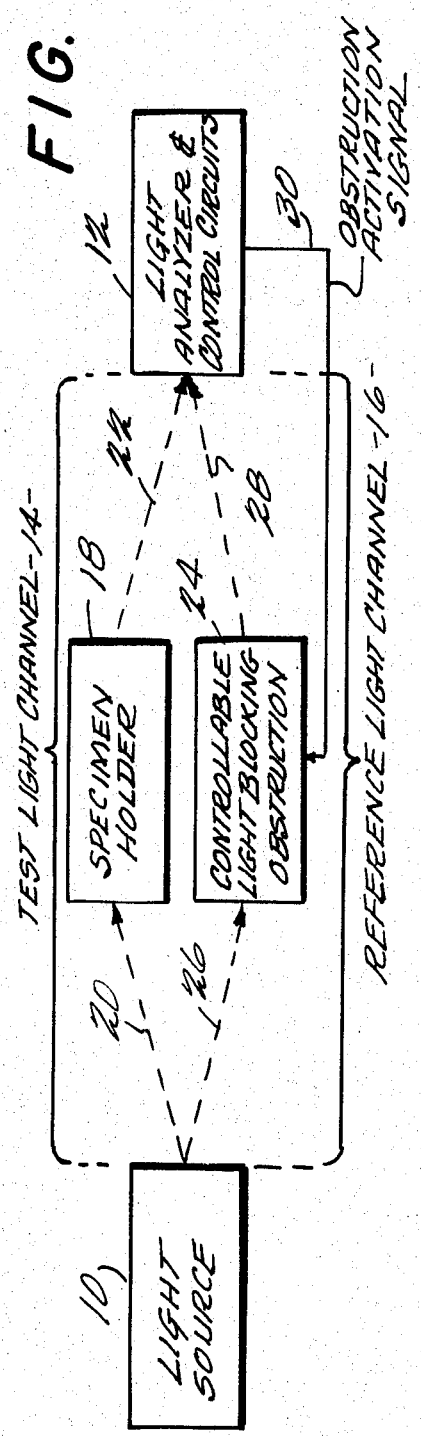
FIG. 1 is block diagram of the presently preferred exemplary embodiment of the apparatus for practice of this invention.

In the exemplary embodiment of apparatus depicted at FIG. 1, a common light source 10 and a common light analyzer and control circuits 12 are employed for both a test light channel 14 and a reference light channel 16. The test light channel 14 emanates from light source 10 to (in the case of reflectance measurements) and/or through (in the case of transmittance measurements) a material specimen held in a specimen holder 18. Conventional lenses, light pipes, fiber optics, etc., may be utilized for defining the test projection optics 20 (e.g., for conducting light flux from the source 10 to the specimen at 18) and for the test viewing optics 22 (i.e., for conducting light flux from the specimen at 18 to the common light analyzer and control circuits 12).

The reference light channel 16 includes a controllable obstruction 24 interposed between its own projection optics 26 and viewing optics 28. In the exemplary embodiment, the latter projection and viewing optics comprise fiber optic bundles. The controllable light blocking obstruction 24 is controlled by an activation signal provided by the light analyzer and control circuits 12 on control line 30. Accordingly, the light analyzer and control circuits may selectively block the reference light channel 16 so as to view light flux emanating through the test light channel 14 alone. Or, alternatively, the light analyzer and control circuits 12 may leave the reference light channel 16 unblocked so as to simultaneously view light flux emanating through both the test light channel 14 and the reference light channel 16.

Figure 2:
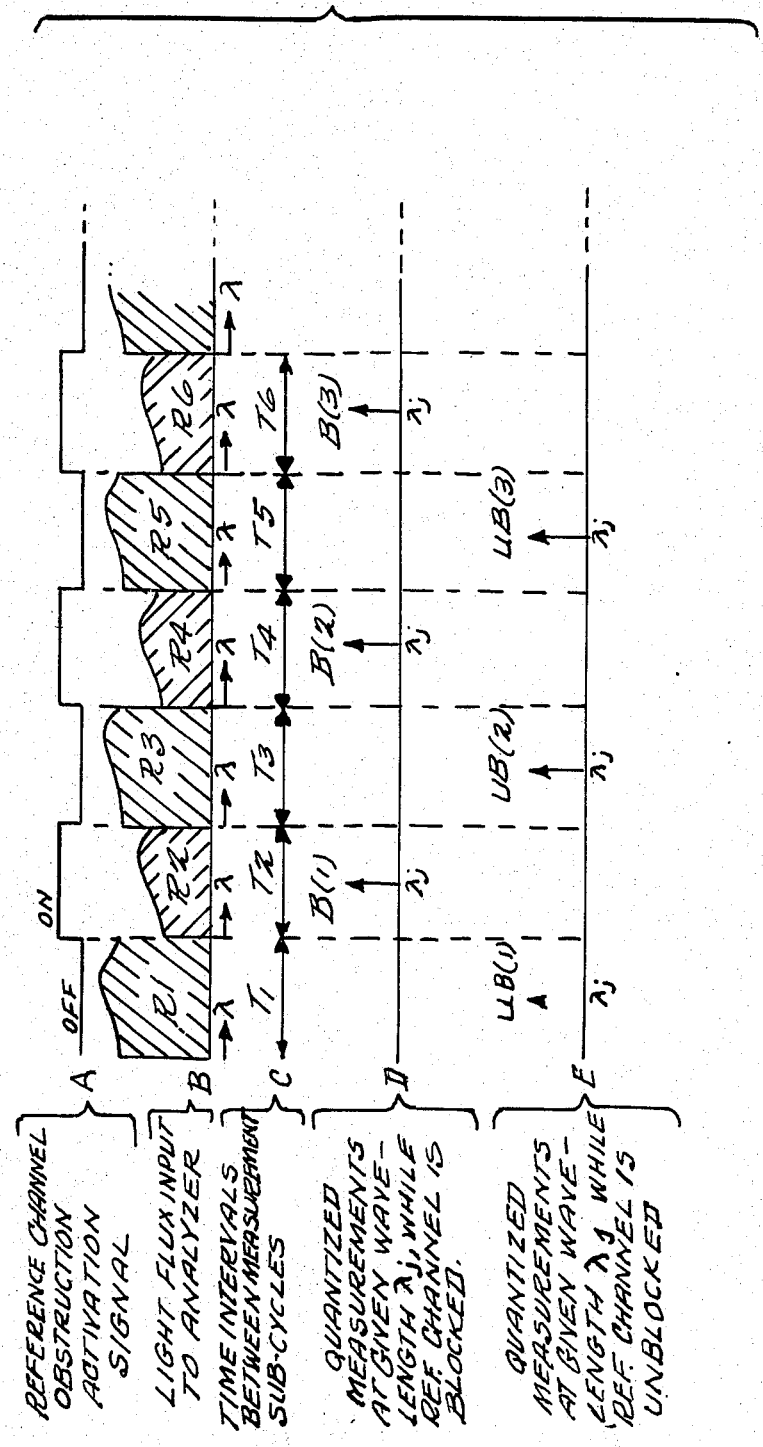
FIG. 2 is a signal-time diagram useful in explaining the operation of the embodiment shown in FIG. 1.

This type of alternating "off" and "on" control of the light blocking mechanism 24 is depicted at line A in FIG. 2. Although many possible modes of operation might be employed, in the exemplary embodiment, the reference channel is left in one of its two states sufficiently long for the light analyzer and control circuits 12 to capture quantitative light flux measurement data at each wavelength of interest. Accordingly, in this particular implementation, the alternate activation periods for the obstruction 24 are relatively long (e.g., on the order of 0.8 seconds).

As should now be apparent, when the reference channel 16 is blocked, relatively less light is input to the light analyzer 12 and this fact is indicated at line B of FIG. 2. As previously indicated, during each measurement cycle, quantitative data measurements are taken at each of many different wavelengths. The successive measurement data B (taken at a given wavelength $\lambda_j$ while the reference channel is blocked) are depicted at line D of FIG. 2 while similar quantitized measurement data UB (taken at that same wavelength while the reference channel is unblocked) are depicted at line E of FIG. 2.

While the operator of the spectrophotometer apparatus is positioning the specimen within holder 18 (or changing its position), the data readings are likely to be spurious. In the exemplary embodiment, similar data taken during successive measurement cycles is compared to be sure that it is approximately the same before quantitative measurements are calculated and accumulated. Thus, a test may be made by subtracting successive data B in ensuring that the difference is less than some predetermined factor X (representing the maximum anticipated noise of the system). Alternatively or additionally, a similar test may be made for successive values of data UB. Once either or both of these tests have been satisfied, it may then be assumed that the specimen is statically located within holder 18. When these tests are satisfied, the derived (UB-B) data truly represents the light flux from the reference channel alone because the test channel light flux has remained constant for at least the last complete measurement cycle.

Figure 3:
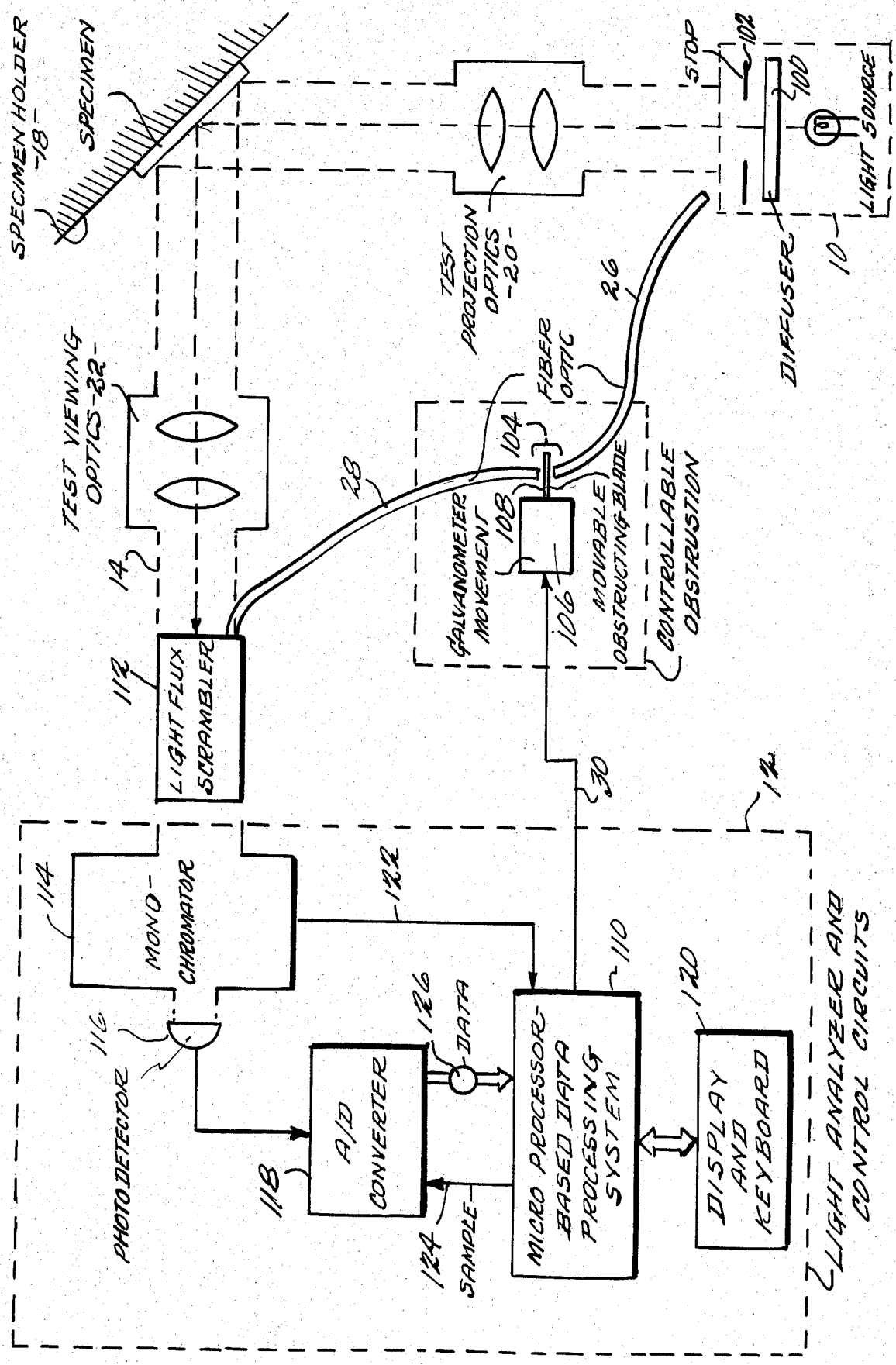
FIG. 3 is a more detailed schematic diagram of the exemplary embodiment shown in FIG. 1.

The more detailed diagram of exemplary apparatus depicted in FIG. 3 is still simplified in several respects as should be apparent to those skilled in the art. Accordingly, it should be understood that various beam splitters may be employed so as to combine parts of the various optical paths shown and that provisions may be made for holding the specimen either in a reflectance position (as shown) or in a transmission position. Those skilled in the art of designing spectrophotometers will recognize many such possible variations and modifications; however, it is believed that the schematic illustration shown in FIG. 3 is adequate for a full understanding and appreciation of the novel features of this invention.

As shown in FIG. 3, the light source 10 typically includes a diffuser 100 and an aperture defining stop member 102. A fiber optic light pipe collects a percentage of the illumination emanating from the light source 10. The presence of diffuser 100 ensures that light collected by the fiber optic bundle 26 is truly representative of the light directed toward the specimen by the projection optics. The diffuser therefore acts to homogenize the light flux emanating from the source.

The collected reference light is then conducted to a small air gap 104 formed by the aligned opposing ends of light fibers 26 and 28. At gap 104, is a small galvanometer 106 having an opaque blade 108 attached to its movement. The galvanometer acts as an optical switch that is capable of blocking the conducted radiation and thus preventing it from crossing the gap 104. Control of the galvanometer is via an activation signal on line 30 generated by a microprocessor-based data processing system 110 in the light analyzer and control circuits 12.

When the gap 104 is unblocked, light flux continues through the remaining section 28 of light fiber and terminates at the input of an optical scrambler 112. The light scrambler 112 may not be needed if the light analyzer employed has uniform response characteristics over its entire input aperture. However, if that is not the case, it is preferable to employ a light flux scrambler 112 at the entrance of the light analyzer 12 (it may be thought of as part of the light analyzer devices) so as to spatially spread light flux from optical fiber 28 to more uniformly fill the input aperture of a conventional monochromator 114. Of course, if the test light channel 14 is not of substantially the same size as the input aperture of the monochromator 114 (e.g., in the case where fiber optics may be utilized to form part of the test light channel), then it may also be desirable to have the light flux scrambler 112 to spread the light flux from the test channel more evenly over the input aperture of the monochromator 114.

Because the light from the light source is non-coherent, the optical power presented to the monochromator via the light scrambler 112 is the sum of optical power conducted through the test and reference channels at each wavelength—that is, there is no significant interference effect as might be the case if coherent light sources are utilized.

In the exemplary embodiment, the light flux scrambler 112 may be realized as a light pipe formed from acrylic plastic having a cross-section substantially the same as that of the monochromator's input aperture. The length of this scrambler is preferably long enough so as to allow light flux from the fiber 28 to completely fill the input aperture of the monochromator 114. In the simplest case, similar light mixing and spreading functions can be achieved by simply providing sufficient space between the input of the monochromator and the output end of the light fiber 28 as should be appreciated. The light pipe scrambler 112 is preferred however so as to minimize the loss of light flux and thus to enhance the available sensitivity of the overall apparatus.

Most monochromators exhibit some sensitivity to the spatial distribution of light flux presented to their input apertures. In those instances, some form of light flux scrambler 112 is preferred so as to help ensure that light flux emanating from both the test and reference channels is processed similarly by the monochromator. However, if a particular monochromator is substantially insensitive to the spatial distribution of light flux at its input aperture, then such scrambling or mixing of light flux from the two channels would be unnecessary.

The galvanometer movement 106 may be of a relatively simple, inexpensive and readily available type. For example, Model No. 802FW available from the Electro-Mechanical Instrument Company, Dublin, Pa., is one suitable galvanometer movement.

The fiber optic bundles 26 and 28 are also of conventional design and may, for example, comprise 0.002 inch fibers packed into a circular jacket having an inside diameter of 0.090 inch. This size bundle is small enough for the blade supplied with the above-mentioned galvanometer movement to totally block the gap 104. The spacing of gap 104 is approximately 0.125 inch in the exemplary embodiment.

The schematic depiction of optical elements 20 and 22 as including lenses and the like in FIG. 3 is intended to be merely a schematic representation. Actually, such viewing and/or projection optics may comprise any conventional optical conduits and/or devices such as beam splitters and fiber optic bundles (which can then be merged with the reference fiber optic bundle 28 at the input to scrambler 112).

The hardware elements included in light analyzer and control circuits 12 in the exemplary embodiment are believed to be of substantially conventional design. For example, a conventional scanning monochromator 114 is employed as is a conventional photodetector 116, a conventional analog-to-digital converter 118 and a microprocessor-based data processing system 110 having conventional hardware architecture including a conventional display and keyboard arrangement 120. Although there are virtually a limitless number of possible configurations of such data processing and control circuits, the presently preferred exemplary embodiment utilizes an integrated circuit microprocessor-type 8088 in conjunction with conventional compatible EPROM (16 kilobytes), RAM (4 kilobytes) and various conventional compatible input-output interfaces. The monochromator is of the scanning circular variable filter (CVF) type driven by a motor having a constant angular velocity.

As will be understood in the art, the monochromator 114 may be caused to continuously cycle over a range of wavelengths and to provide a synchronizing signal on line 122 each time a new scan of the available wavelength ranges is initiated (or completed). Conventional analog-to-digital converter 118 typically is caused to capture (e.g., "sample and hold") a sample of the input analog signal in response to a control signal on line 124 and, in response, to provide a digital data word or byte representative thereof on lines 126. Conventional I/O circuits are also utilized for generating the activation control signal on line 30 for the galvanometer movement 106.

Typically, overall machine operation is controlled by an operator via a keyboard 120 and data results are communicated via either printed or visual displays to the operator. Since the electrical hardware architecture of the microprocessor-based data processing system depicted in FIG. 3 is believed to be conventional, no further detailed description is believed necessary.

One exemplary embodiment for relevant portions of a controlling program to be used in conjunction with the microprocessor of FIG. 3 is depicted at FIGS. 4 and 5. It should be understood that there are many alternate sequences and/or organizations of program steps which might be employed to achieve similar end results.

In the exemplary embodiment, the monochromator 114 scans through a range of approximately 10 nanometers of optical wavelength in a 10-millisecond time interval. Since this is one convenient wavelength increment, the exemplary system is organized so as to provide time interrupts to the microprocessor every 10 milliseconds.

Whenever such a time interrupt occurs, control of the microprocessor is transferred to a time interrupt program such as that shown in FIG. 4. Here, immediately after entry, digital data B or UB from the A/D converter 118 (and ultimately from the photodetector 116) are captured and stored in an appropriate memory location corresponding to a particular wavelength W(j). Of course, if the reference channel is then blocked (e.g., as represented by the status of a "block" flag data register), then B data is captured. Alternatively, if the reference channel is unblocked, then UB data is captured. Thereafter, the wavelength counter j is incremented at 402 and a test is made at 404 to see if a complete measurement cycle has been completed (i.e., whether a measurement at the maximum wavelength has yet been captured. If not, an immediate return to the main program from the timed interrupt sub-routine is made as indicated at 406.

If data has now been captured for the maximum wavelength at which it is to be measured, then the wavelength counter is reset at 408 and a test is made at 410 to see if the reference channel is blocked. If it is, then the reference channel is unblocked at 412 and the block flag is reset. If not, then the reference channel is blocked at 414 and the block flag is set. Thereafter, a "cycle" flag may be incremented (or alternated to another value) at 416 to indicate that a complete measurement cycle has now been completed. A wait loop is then entered at 418 until a synchronization signal on line 122 is received from the monochromator 114 indicating that a new cycle of the monochromator has been initiated. Once such a new cycle has been initiated, then the timing circuitry which causes timed interrupts at 10-millisecond intervals is restarted at 420 so as to ensure continued synchronization of the timed-interrupt sub-routine with the monochromator 114. Thereafter, a normal return is made at 422 to the main control program.

The exemplary main control program depicted in FIG. 5 has been abbreviated so as to portray only those portions of the program that are relevant to an understanding of the novel features of this invention.

Immediately after the microprocessor circuits are energized, the various data and control registers, flags, etc., are initialized at step 500. The "cycle" flag is tested at 504 to see if a new measurement cycle has yet been completed. If not, then a wait loop is entered around test step 504. Eventually, when a new measurement cycle has been completed, test step 506 will be encountered. Here, two successive UB data values are subtracted and the absolute difference is compared to the maximum expected noise of the system to be sure that the specimen is stationary in its holder. For example, differences greater than approximately 0.1% of one of the measured data values (or of an average of them) might in some systems be an indication that additional settling time is required. If so, the (UB-B) data is invalid as a measure of the reference channel light flux and therefore step 514 is skipped. A similar test may be made on B data values as indicated at test step 508. As should be appreciated, one or both of the tests 506 and 508 may be eliminated in some applications. At step 514, the (UB-B) derived data representing the magnitude of light flux emanating through the reference channel alone is computed. This data is then accumulated by a running average filter and the resulting filtered version of (UB-B) is stored in register R.

The thus-averaged derived difference data values are then used in the drift-correction calculation using test channel data B that may or may not be averaged in a similar way as desired. It will be understood that the time constant of such an averaging filter should be short compared to the anticipated drift rate that is to be corrected. Although such averaging is preferred, it is not believed to be required for acceptable system operation.

When the averaging techniques previously discussed are used, it is also preferable for the optic circuits to be designed such that very little light reflected from the specimen is collected by the reference light fiber through various unwanted light paths which can nevertheless often not be completely eliminated. If significant reflected light from the test specimen is somehow included in the reference channel, then the reference signal will be dependent upon the specimen. In such cases, averaging of the (UB-B) data is not preferred because the effective illumination provided by the source is different for different specimens. Therefore, the most recently computed (UB-B) data should be used to compute C in order to ensure accurate results. However, the exemplary preferred embodiment of the invention continually measures and filters the derived (UB-B) reference channel data except when test specimens are being removed from or affixed to the specimen holder.

At step 516, corrected data C is computed by dividing data B by the filtered derived difference data R for each of the several wavelengths. At step 518, the corrected data C is further multiplied by the previously stored standardization scale factors for each of the various wavelengths so as to obtain final standardized corrected data values referenced to a standard specimen. The final results are then displayed and/or stored as desired at 520 before a return is made to point A in the program to begin a completely new cycle of analysis.

It should now be appreciated that the drift-corrected data reading is independent of scale changes caused by variations in critical parameters of components common to both the test and reference light channels. For example, these would include the common light source, monochromator, photodetector(s), electronics and any other optical components (e.g., leveling filters) common to both paths. Of course, standardization of the drift-corrected data must still be done in the conventional manner as previously explained using stored pre-calculated standardization scale factors for each particular wavelength.

While only one exemplary embodiment has been described in detail, those skilled in the art will readily appreciate that there are many possible variations and modifications that can be made in this exemplary embodiment without materially departing from many of its novel features and advantages. Accordingly, all such variations and modifications are intended to be included within the scope of the following appended claims.

What is claimed is:

1. Spectrophotometer apparatus comprising:
   a light source;
   a light analyzer;
   a specimen testing light conducting channel emanating from said light source, terminating at said light analyzer and including means for introducing a specimen to be tested into its light conducting path, which path continuously conducts light flux over a complete analyzing cycle; and
   a reference light conducting channel emanating from said light source, terminating at said light analyzer and including blocking means for temporarily occluding its light conducting path during an analyzing cycle;
   wherein said light analyzer includes means for quantitatively detecting and measuring light flux input thereto and means for subtracting the measurement obtained when the reference channel is occluded from that obtained when the reference channel is not occluded to thus derive a quantitative measure of the light flux being conducted through the reference channel alone; and
   wherein said light analyzer includes means for drift-correcting the test measurement obtained when the reference channel is occluded by use of said derived quantitative measure of the light flux being conducted through the reference channel alone.

2. Spectrophotometer apparatus comprising:
   a light source;
   a light analyzer;
   a specimen testing light conducting channel emanating from said light source, terminating at said light analyzer and including means for introducing a specimen to be tested into its light conducting path, which path continuously conducts light flux over a complete analyzing cycle; and
   a reference light conducting channel emanating from said light source, terminating at said light analyzer and including blocking means for temporarily occluding its light conducting path during an analyzing cycle;
   wherein said light analyzer includes:
      a monochromator disposed to intercept incident light flux from both said light conducting channels and to pass only a predetermined band of wavelengths therethrough;

a photodetector means disposed to intercept light flux passed by said monochromator and to provide corresponding quantitative electrical measurement signals in response thereto; and data processing and control means electrically connected to receive said quantitative electrical measurement signals and to control said blocking means so as to obtain a relative measurement of a specimen's optical properties substantially unaffected by changes which may occur from time-to-time in said light source and in said light analyzer.

3. Spectrophotometer apparatus as in claim 2 further comprising light scrambler means for spatially mixing light flux from both said light conducting channels as it is input to said light analyzer.

4. Spectrophotometer apparatus as in claim 2 wherein said reference light conducting channel comprises a fiber optic light conduit.

5. Spectrophotometer apparatus as in claim 2 wherein said reference light conducting channel comprises a serially arranged pair of fiber optic light conduits having a pair of respective aligned ends which define a gap in which said blocking means is interposed.

6. Spectrophotometer apparatus as in claim 5 wherein said blocking means comprises a physical light blocking member which can be selectively moved into and out of said gap upon electrical activation.

7. Spectrophotometer apparatus as in claim 2 wherein said light analyzer includes means for (1) capturing data B representing the quantity of light flux received when the reference channel is blocked, (2) capturing data UB representing the quantity of light flux received when the reference channel is unblocked and (3) calculating drift-corrected measurement data $C = B/(UB-B)$.

8. Spectrophotometer apparatus as in claim 2 wherein said light analyzer includes means for taking data during cyclic sample periods when said reference channel is blocked and when it is unblocked and wherein said light analyzer also includes means for inhibiting quantitative analysis of such collected data unless data collected during successive similar portions of such cylic sample periods agree within a predetermined tolerance value.

9. Spectrophotometer apparatus as in claim 2 wherein said light analyzer includes means for taking data during cyclic sample periods when said reference channel is blocked and when it is unblocked and wherein said light analyzer also includes means for averaging together derived data over plural of the most recent cyclic sample periods before providing a final quantitative output measurement.

10. Spectrophotometer apparatus as in claim 7 wherein said reference light conducting channel comprises a pair of fiber optic light conduits having a pair of respective aligned ends which define a gap in which said blocking means is interposed.

11. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle;
a reference light conducting channel emanating from said light source, terminating at said light analyzer and including blocking means for temporarily occluding its light conducting path during an analyzing cycle; and light scrambler means for spatially mixing light flux from both said light conducting channels as it is input to said light analyzer.

12. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle; and
a reference light conducting channel emanating from said light source, terminating at said light analyzer and including blocking means for temporarily occluding its light conducting path during an analyzing cycle;
wherein said reference light conducting channel comprises a fiber optic light conduit.

13. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle; and
a reference light conducting channel emanating from said light source, terminating at said light analyzer and including blocking means for temporarily occluding its light conducting path during an analyzing cycle;
wherein said reference light conducting channel comprises a serially arranged pair of fiber optic light conduits having a pair of respective aligned ends which define a gap in which said blocking means is interposed.

14. Spectrophotometer apparatus as in claim 13 wherein said blocking means comprises a physical light blocking member which can be selectively moved into and out of said gap upon electrical activation.

15. Spectrophotometer apparatus as in claim 14 wherein said blocking means comprises a blade attached to the movement of a galvanometer.

16. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle; and
a reference light conducting channel emanating from said light source, terminating at said light analyzer and including blocking means for temporarily occluding its light conducting path during an analyzing cycle;
wherein said light analyzer includes means for (1) capturing data B representing the quantity of light flux received when the reference channel is blocked, (2) capturing data UB representing the quantity of light flux received when the reference channel is unblocked and (3) calculating drift-corrected measurement data $C = B/(UB-B)$.

17. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle; and
a reference light conducting channel emanating from said light source, terminating at said light analyzer and including blocking means for temporarily occluding its light conducting path during an analyzing cycle;
wherein said light analyzer includes means for taking data during cyclic sample periods when said reference channel is blocked and when it is unblocked and wherein said light analyzer also includes means for inhibiting quantitative analysis of such collected data unless data collected during successive similar portions of such cyclic sample periods agree within a predetermined tolerance value.

18. Spectrophotometer apparatus comprising:
a light source;
a light analyzer;
a specimen testing light conducting channel emanating from said light source, terminating at said light analyzer and including means for introducing a specimen to be tested into its light conducting path, which path continuously conducts light flux over a complete analyzing cycle; and
a reference light conducting channel emanating from said light source, terminating at said light analyzer and including blocking means for temporarily occluding its light conducting path during an analyzing cycle;
wherein said light analyzer includes means for taking data during cyclic sample periods when said reference channel is blocked and when it is unblocked and wherein said light analyzer also includes means for averaging together derived data over plural of the most recent cyclic sample periods before providing a final quantitative output measurement.

19. Spectrophotometer apparatus comprising:
a source of light flux;
a specimen holding means for holding a specimen having optical properties to be tested;
light analyzing means for quantitatively measuring light flux incident thereon at different wavelengths;
an unobstructed test light transmitting means for conducting light flux from said source to said light analyzing means via said specimen holding means so that the light flux transmitted to the analyzing means is affected by the optical properties of said specimen;
a reference light transmitting means for conducting light flux from said source to said light analyzing means; and
said reference light transmitting means including a controllable light flux obstruction means for temporarily occluding said reference light transmitting means upon activation.

20. Spectrophotometer apparatus as in claim 19 wherein said light analyzing means comprises:
a monochromator disposed to intercept said incident light flux and to pass only selected wavelengths therethrough as determined by applied electrical control signals;
a photodetector disposed to intercept light flux passed by said monochromator and to provide analog electrical output signals in response thereto;
an analog-to-digital converter connected to said photodetector for providing digital electrical ouput signals corresponding to said analog signals; and
digital data processing means electrically connected to said analog-to-digital converter and to said obstruction means for analyzing successive of said digital signals during successive time intervals when said obstruction means is activated and not activated so as to obtain a relative measurement of said specimen's optical properties substantially unaffected by parameter changes which may occur from time-to-time in said source of light flux and in said light detecting means.

21. Spectrophotometer apparatus as in claim 19 or 20 further comprising a light scrambler means for spatially mixing the light flux emanating from both the test and reference light transmitting means as it is input to said light analyzing means.

22. Spectrophotometer apparatus as in claim 19 or 20 wherein said reference light transmitting means comprises a fiber optic conduit.

23. Spectrophotometer apparatus as in claim 19 or 20 wherein said reference light transmitting means comprises a pair of fiber optic conduits which define a gap by substantially aligned spaced apart ends thereof and wherein said controllable light flux obstruction means comprises a light interrupting obstruction which can be selectively moved into and out of said gap upon electrical activation.

24. Spectrophotometer apparatus as in claim 23 wherein said controllable light flux obstruction means comprises a blade attached to a galvanometer device.

25. Spectrophotometer apparatus as in claim 19 or 20 wherein said light analyzing means captures data B representing the quantity of light flux received when the reference light transmitting means is blocked, captures data UB representing the quantity of light flux received when the reference light transmitting means is unblocked and calculates drift-corrected data C=B/(UB-B) representing the quantity of light flux received from the test light transmitting means.

26. Spectrophotometer apparatus as in claim 25 wherein said light analyzing means also compares said data B captured during one sample period with that captured during a subsequent sample period and which then inhibits further quantitative analysis of the captured data unless the compared data are within a predetermined tolerance of similar values.

27. Spectrophotometer apparatus as in claim 25 wherein said light analyzing means also compares said data UB captured during one sample period with that captured during a subsequent sample period and which then inhibits further quantitative analysis of the captured data unless the compared data are within a predetermined tolerance of similar values.

28. Spectrophotometer apparatus as in claim 25 wherein at least one of said data B and UB represents an average of data accumulated over plural sampling periods.

29. Spectrophotometer apparatus as in claim 26 wherein at least one of said data B and UB represents an average of data accumulated over plural sampling periods.

30. Spectrophotometer apparatus as in claim 27 wherein at least one of said data B and UB represents an average of data accumulated over plural sampling periods.

31. Spectrophotometer apparatus as in claim 25 wherein the difference data UB-B represents an average of such difference data accumulated over plural sampling periods.

32. Spectrophotometer apparatus as in claim 26 wherein the difference data UB-B represents an average of such difference data accumulated over plural sampling periods.

33. Spectrophotometer apparatus as in claim 27 wherein the difference data UB-B represents an average of such difference data accumulated over plural sampling periods.

34. Spectrophotometer method employing a light source and a light analyzer, said method comprising the steps of:
   introducing a specimen to be tested into a light conducting path emanating from said source to said analyzer, which path continuously conducts light flux over a complete analyzing cycle;
   temporarily occluding a reference light conducting path also emanating from said source to said analyzer during an analyzing cycle;
   quantitatively detecting and measuring light flux input to the analyzer and subtracting the measurement obtained when the reference channel is occluded from that obtained when the reference channel is not occluded to thus derive a quantitative measure of the light flux being conducted through the reference channel alone; and
   drift-correcting the test measurement obtained when the reference channel is occluded by use of said derived quantitative measure of the light flux being conducted through the reference channel alone.

35. Spectrophotometer method employing a light source and a light analyzer, said method comprising the steps of:
   introducing a specimen to be tested into a light conducting path emanating from said source to said analyzer, which path continuously conducts light flux over a complete analyzing cycle;
   temporarily occluding a reference light conducting path also emanating from said source to said analyzer during an analyzing cycle;
   quantitatively detecting and measuring light flux input to the analyzer and subtracting the measurement obtained when the reference channel is occluded from that obtained when the reference channel is not occluded to thus derive a quantitative measure of the light flux being conducted through the reference channel alone; and
   wherein said quantitatively detecting and measuring light flux step comprises taking data during cyclic sample periods when said reference channel is blocked and when it is unblocked and inhibiting quantitative analysis of such collected data unless data collected during successive similar portions of such cyclic sample periods agree within a predetermined tolerance value.

36. Spectrophotometer method employing a light source and a light analyzer, said method comprising the steps of:
   introducing a specimen to be tested into a light conducting path emanating from said source to said analyzer, which path continuously conducts light flux over a complete analyzing cycle;
   temporarily occluding a reference light conducting path also emanating from said source to said analyzer during an analyzing cycle;
   quantitatively detecting and measuring light flux input to the analyzer and subtracting the measurement obtained when the reference channel is occluded from that obtained when the reference channel is not occluded to thus derive a quantitative measure of the light flux being conducted through the reference channel alone; and
   wherein said quantitatively detecting and measuring light flux step comprises taking data during cyclic sample periods when said reference channel is blocked and when it is unblocked and averaging together derived data over plural of the most recent cyclic sample periods before providing a final quantitative output measurement.

37. Spectrophotometer method employing a light source and a light analyzer, said method comprising the steps of:
   introducing a specimen to be tested into a light conducting path emanating from said source to said analyzer, which path continuously conducts light flux over a complete analyzing cycle;
   temporarily occluding a reference light conducting path also emanating from said source to said analyzer during an analyzing cycle; and
   spatially mixing light flux from said light conducting channels as it is input to said light analyzer.

38. Spectrophotometer method employing a source of light flux, a specimen holding means for holding a specimen having optical properties to be tested and a light analyzing means for quantitatively measuring light flux incident thereon at different wavelengths, said method comprising the steps of:
   continuously conducting light flux from said source to said light analyzing means via said specimen holding means over a complete analyzing cycle so that the light flux thus continuously transmitted to the analyzing means is affected by the optical properties of said specimen;
   cyclically conducting light flux from said source to said light analyzing means via a reference light transmitting means including a controllable light flux obstruction means which is controlled to temporarily occlude said reference light transmitting means;
   intercepting said incident light flux with a monochromator and passing only selected wavelengths therethrough as determined by applied electrical control signals;
   intercepting light flux passed by said monochromator with a photodetector and providing analog electrical output signals in response thereto;
   providing digital electrical output signals corresponding to said analog signals; and
   analyzing successive of said digital signals during successive time intervals when said obstruction means is activated and not activated so as to obtain a relative measurement of said specimen's optical properties substantially unaffected by parameter changes which may occur from time-to-time in said source of light flux and in said light detecting means.

39. Spectrophotometer method employing a source of light flux, a specimen holding means for holding a specimen having optical properties to be tested and a light analyzing means for quantitatively measuring light flux incident thereon at different wavelengths, said method comprising the steps of:

continuously conducting light flux from said source to said light analyzing means via said specimen holding means over a complete analyzing cycle so that the light flux thus continuously transmitted to the analyzing means is affected by the optical properties of said specimen;

cyclically conducting light flux from said source to said light analyzing means via a reference light transmitting means including a controllable light flux obstruction means which is controlled to temporarily occlude said reference light transmitting means; and spatially mixing the light flux emanating from both the test and reference light transmitting means as it is input to said light analyzing means.

40. Spectrophotometer method employing a source of light flux, a specimen holding means for holding a specimen having optical properties to be tested and a light analyzing means for quantitatively measuring light flux incident thereon at different wavelengths, said method comprising the steps of:

continuously conducting light flux from said source to said light analyzing means via said specimen holding means over a complete analyzing cycle so that the light flux thus continuously transmitted to the analyzing means is affected by the optical properties of said specimen;

cyclically conducting light flux from said source to said light analyzing means via a reference light transmitting means including a controllable light flux obstruction means which is controlled to temporarily occlude said reference light transmitting means;

capturing data B representing the quantity of light flux received when the reference light transmitting means is blocked, capturing data UB representing the quantity of light flux received when the reference light transmitting means is unblocked, and calculating drift-corrected data $C = B/(UB-B)$ representing the quantity of light flux received from the test light transmitting means.

41. Spectrophotometer method as in claim 40 further comprising the steps of:

comparing said data B captured during one sample period with that captured during a subsequent sample period and then inhibiting further quantitative analysis of the captured data unless the compared data are within a predetermined tolerance of similar values.

42. Spectrophotometric method as in claim 40 further comprising the steps of:

comparing said data UB captured during one sample period with that captured during a subsequent sample period and then inhibiting further quantitative analysis of the captured data unless the compared data are within a predetermined tolerance of similar values.

43. Spectrophotometric method as in claim 40 wherein at least one of said data B, UB and UB-B represents an average of data accumulated over plural sampling periods.

44. Spectrophotometric method as in claim 41 wherein at least one of said data B, UB and UB-B represents an average of data accumulated over plural sampling periods.

45. Spectrophotometric method as in claim 42 wherein at least one of said data B, UB and UB-B represents an average of data accumulated over plural sampling periods.

* * * * *